United States Patent [19]

Black et al.

[11] Patent Number: 5,420,280

[45] Date of Patent: May 30, 1995

[54] PIPERIDIN-4-SPIRO-OXIRANES

[75] Inventors: Robin M. Black; Keith Brewster, both of London, England

[73] Assignee: The Secretary of State for Defence in Her Britannic Majesty's Government of the United Kingdom of Great Britain and Northern Ireland, London, United Kingdom

[21] Appl. No.: 937,821

[22] PCT Filed: Apr. 5, 1990

[86] PCT No.: PCT/GB91/00531

§ 371 Date: Oct. 20, 1992

§ 102(e) Date: Oct. 20, 1992

[87] PCT Pub. No.: WO91/15492

PCT Pub. Date: Oct. 17, 1991

[30] Foreign Application Priority Data

Apr. 5, 1990 [GB] United Kingdom ............... 9007724

[51] Int. Cl.$^6$ .................. C07D 221/20; C07D 211/40
[52] U.S. Cl. ...................... 546/16; 546/216; 546/223; 546/224; 546/233
[58] Field of Search .............. 546/16, 216, 223, 233, 546/224

[56] References Cited

PUBLICATIONS

McOmis "Protective Groups in Organic Chemistry" Plenum Press, p. 61 (1974).
Satoh et al "α-β-Epoxy Sufoxides as Intermediates in Organic Synthesis II" Chem. Soc. Japan, 58 2849-54 (1985) (cited on PCT Search Report).
Satoh et al "A Novel Approach to Synthesis of Chiral Epoxides" Tetra. Lett. 29 2851-2854 (1988).
Satoh et al "A Novel Method of Annulation of αβ-- Epoxid Sulfoxide" Chem. Lett Japan, 1949-50 (1987).
Satoh et al "A Novel Synthesis of 2 Acrylic Ether . . . " Bull. Chem. Soc. Jpn. 61 2109-2115 (1988).

*Primary Examiner*—Celia Chang
*Attorney, Agent, or Firm*—Nixon & Vanderhye

[57] ABSTRACT

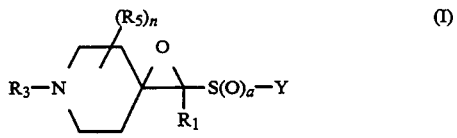

Novel piperidin-4-spiro-oxiranes of formula (I) are provided which have application in the synthesis of various anilidopiperidine compounds. The novel compounds can be synthesised in a one pot reaction from 4-substituted piperidones and phenylsulphoxide or sulphone starting materials. Use of the novel compounds allows anilidopiperidines to be produced in a significantly reduced number of stages than with previously known methods.

6 Claims, 2 Drawing Sheets

PIPERIDIN-4-SPIRO-OXIRANES

The present invention relates to novel piperidin-4-spiro-oxirane compounds and to a method for their preparation. The invention further provides a novel method for the preparation of anilidopiperidines using said compounds or incorporating the method for their preparation.

The anilidopiperidines includes the highly useful fentanyl type compounds having potent analgesic and anaesthetic properties which render them useful in major surgical procedures. Particularly useful and well known examples of these compounds are the drugs Sufentanil and R.30.490 both of which have high potency yet good safety ratios as defined by the ratio $ED_{50}/LD_{50}$ as determined in rats.

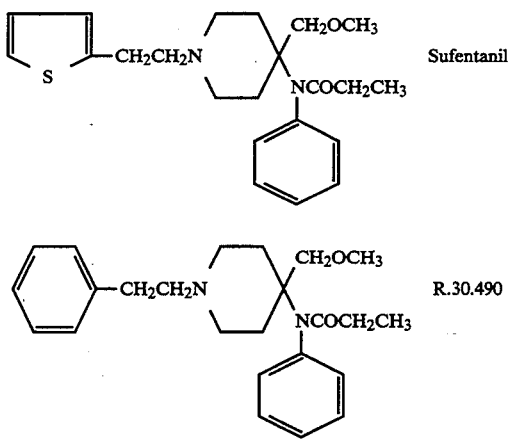

Other related compounds are also known eg: 4-keto analogues where the 4-alkoxyalkyl substitutent of the piperidine is replaced by keto groups as described in U.S. Pat. No. 4,179,569.

A disadvantage of all these compounds is the lengthy multistage synthesis required to prepare them from readily available starting materials. Previously reported procedure (Refs 1 and 2) for the preparation of Sufentanil involves a nine stage synthesis from 1-benzyl-4-piperidone (see FIG. 1). A similar multistage process is reported in U.S. Pat. No. 4,179,569 and Drugs Future 5 p410–411 (1980) for the synthesis of R.30.490 starting from 1-benzyl piperidone. It is clear that an alternative, shorter synthetic route would reduce manufacturing costs considerably.

Figure 1:
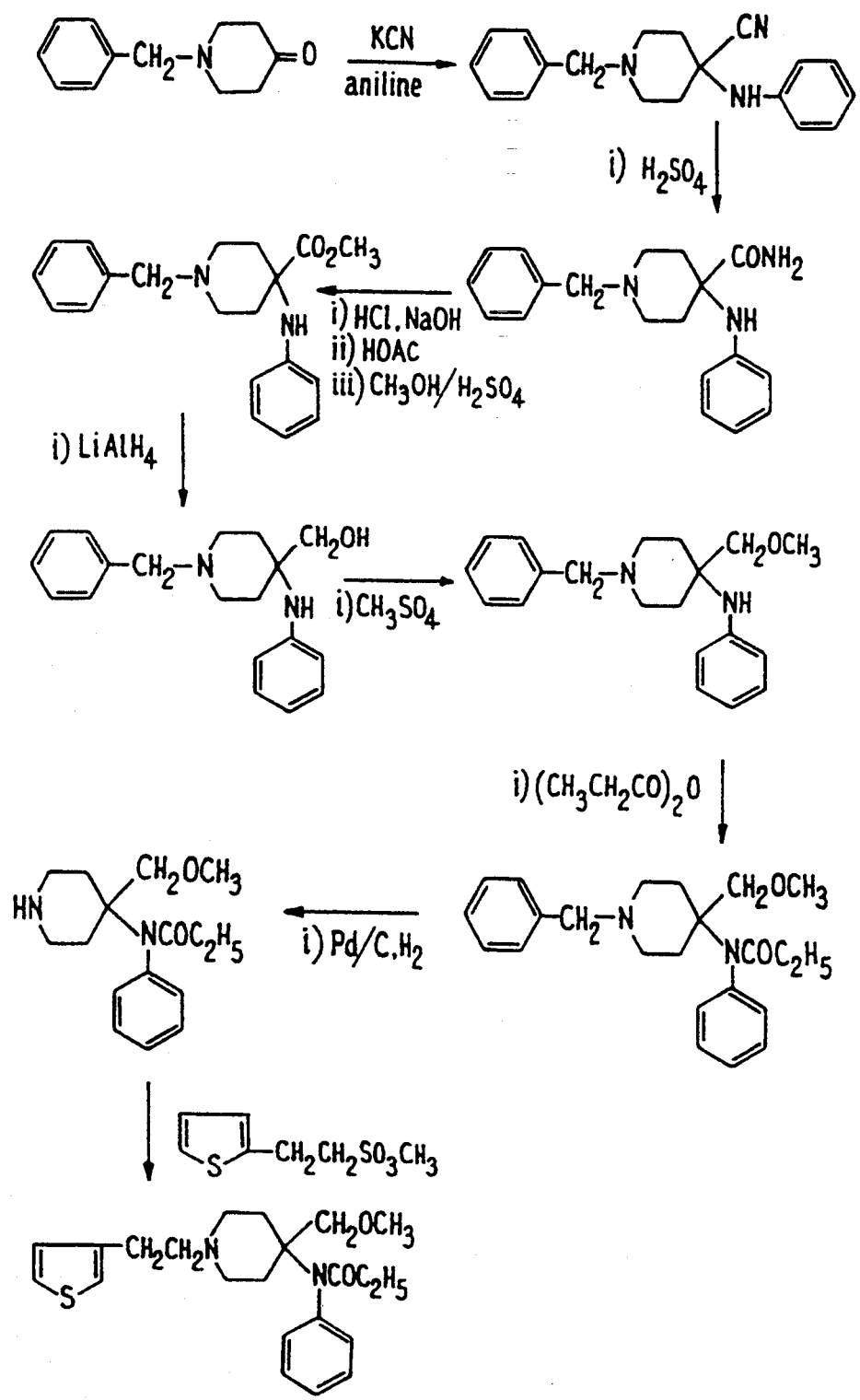
In FIGS. 1 and 2, the synthetic route for making disclosed compounds are shown.

The present invention provides such a route via novel piperidin-4-spiro-oxiranes of general formula (I).

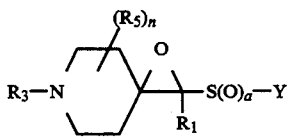

Wherein
$R_1$ is a hydrogen atom or an optionally substituted alkyl alkenyl, aryl or arylalkyl group $R_3$ is a hydrogen atom or an optionally substituted alkyl, alkenyl, arylalkyl, alkoxyalkyl, aryloxyalkyl or heterocyclyalkyl group $R_5$ is an optionally substituted alkyl or hydroxy group or a halogen, sulphonic, nitro, cyano or trifluoromethyl group.

Y is an optionally substituted alkyl, alkenyl, aryl, cycloalkyl, or heterocyclyl group n is 0 or an integer from 1 to 8 with $R_5$ being independently selected for each substitution such that where n is greater than 1 each value of $R_5$ may be different, and a is an integer 1 or 2.

Preferably
$R_1$ is hydrogen or an optionally substituted $C_{1-8}$ alkyl $C_{2-8}$ alkenyl, aryl or $C_{7-10}$ arylalkyl group $R_3$ is hydrogen or an optionally substituted $C_{1-8}$ alkyl $C_{2-8}$ alkenyl, aryl, $C_{7-10}$ arylalkyl, $C_{7-10}$ aryloxyalkyl, $C_{4-10}$ alkoxyalkyl, thienylalkyl, furanylalkyl, pyridinylalkyl or indenylalkyl group $R_5$ is an optionally substituted $C_{1-8}$ alkyl or $C_{2-8}$ alkenyl group, a halogen atom or a sulphonic or nitro group Y is an optionally substituted $C_{1-8}$ alkyl or aryl group and n is 0 or an integer from 1 to 4.

Most preferably $R_3$ is an optionally substituted $C_{1-8}$ alkyl, phenylmethylene, phenylethylene, thienylethylene, furanylethylene, pyridinylethylene or indenylethylene group. Most advantageously $R_1$ is hydrogen or $C_{1-3}$ alkyl, $R_3$ is phenylmethyl (benzyl) or 2-phenylethyl, $R_5$ is $C_{1-8}$ alkyl, n is 0, 1 or 2 and Y is optionally substituted alkyl or aryl. When intended for the preparation of anilidopiperines the values of $R_1$, $R_3$ and $R_5$ conveniently correspond to the substitutents on the piperidyl nitrogen of a desired final product eg; for $R_3$ this might be carbocyclic or heterocyclic substituted alkyl groups such as 2-phenylethyl, 2-thienylethyl, 2-furanylethyl, 2-pyridinylthyl or 2-indenylethyl groups or their substituted analogues for synthesis of fentanyls of compounds described in U.S. Pat. No. 4,179,569 eg; 2-thienylethyl in the case of sufentanil or 2-phenyl ethyl in the case of R.30.490.

Alternatively $R_1$, $R_3$ and $R_3$ may be selected such that the final product may be conveniently be synthesised with respect to them ie: they may be selected as protecting groups or as intermediates. Expensive reagents such as those used to form the thienylethylene group might be advantageously used at the last stage of the synthesis rather than be wasted through yield losses while cheaper benzyl or methyl groups are used to protect the piperidinyl nitrogen in preceeding stages. A final step would for example involve removal of said benzyl group by hydrogenation and then reaction with 2-thienylethylbromide.

The present invention further provides a method for the synthesis of the compounds of the formula (I) wherein:

(a) a compound of general formula (II), wherein $R_3$ and $R_5$ are as defined in formula (I), is reacted with a compound of formula (III), wherein X is a halogen atom and a, Y and $R_1$ are as defined in formula (I) to produce a compound of formula (IV) wherein $R_1$, $R_3$, $R_5$, Y, n and a are as defined in formula (I).

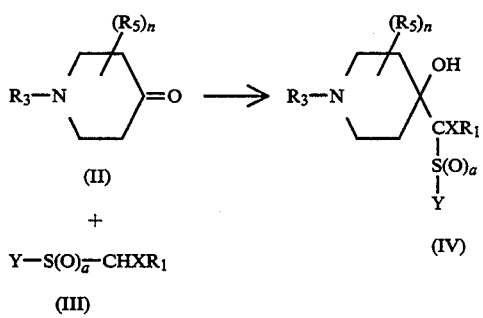

+

Y—S(O)$_{\overline{a}}$—CHXR$_1$ (III)

then (b) the compound of general formula (IV) is converted under basic conditions to a compound of formula (I)

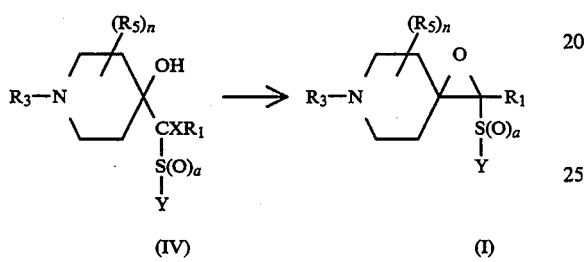

In practice the conversion of the compound of formula (II) to that of one of formula (I) is preferably carried out in one stage in a single reaction vessel without isolation of the formula (IV) intermediate. However, the compounds of formula (IV) may be isolated (eg. Example 11 below) and as they solidify much more readily than the oxiranes, their isolation is possible by precipitation thus giving a further purification option in the oxirane preparation.

The reaction of the compound of formula (II) with that of formula (III) may be carried out under influence of a base in a dry solvent with the exclusion of air (eg;) by use of a nitrogen atmosphere) and at low temperature. In the dry solvent technique the step (b) is typically instigated by use of an organometallic agent, preferably an organo-alkali metal agent, preferably N-butyllithium. The reaction is preferably worked up by pouring the reaction mixture onto water and extracting it into a water immiscible organic solvent; preferably ether, dichloromethane or chloroform. By use of such basic conditions in the reaction medium the cyclisation of the compound of formula (IV) to formula (I) occurs readily but in order to maintain purity reaction is carried out at temperatures below zero, preferably below $-30°$ C., most preferably at temperatures below $-70°$ C., particularly about $-78°$ C.

A second method of producing the compounds of formula (I), preferred for synthesis of sulphones of formula (I) (a is 2), reacts the compounds of formulas (II) and (III) in an organic solvent in the presence of a phase transfer catalyst and an aqueous base (eg. NaOH, KOH or other strong base) solution under agitation conditions. Examples of suitable phase transfer catalysts are tricaprylmethylammonium chloride, Adogen 464(TM) and triethylbenzylammonium chloride. This reaction technique allows use of ambient temperature and may be advantageous for industrial scale production in it's avoidance of hazardous hydride reagents. The reaction is worked up by separation and drying of the organic layer followed by purification techniques.

The third embodiment of the present invention comprises a novel route to the anilidopiperidines comprising use of compounds (I) as starting products of intermediates. The compounds of general formula (I) are readily prepared as outlined above and are then converted to compounds of general formula (V)

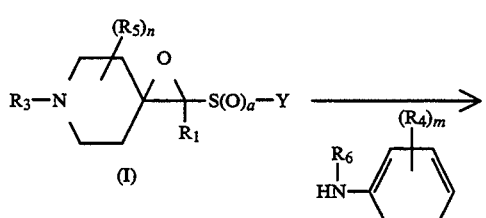

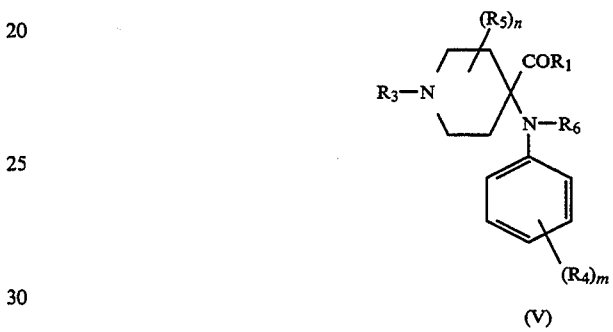

(V)

wherein the compound of formula (I) is reacted with an optionally substituted aniline; $R_1$, $R_3$ and $R_5$, n, a and Y are as previously defined and $R_4$ is halogen, hydroxy, cyano, trifluoromethyl, nitro, sulphonic, or an optionally substituted alkyl, alkenyl or alkoxy group or two $R_4$ moieties may together form a carbocyclic or heterocyclic ring; $R_6$ is hydrogen or optionally substituted alkyl; value m is selected from 0 or an integer from 1 to 5 and $R_4$ may be independently selected at each occurance.

Generally this reaction proceeds at room temperature with a trace of polar organic solvent present eg; dimethylsulphoxide. The compounds of formula (V) open the way to further conversions of known type as summarised in FIG. 2. These include the following examples whereby further intermediates (VI) and (VII) are synthesised. Reduction of a compound of formula (V) eg; using sodium hydride or lithium aluminium hydride gives a compound of formula (VI) which can be alkylated using the general methods of Janssen or by the action of diazoalkanes in the presence of silica or of halogenoalkanes in the presence of a hydride to give compounds of the general formula (VII).

Examples of Synthetic Routes: (see FIG. 2)

(i) N-acylation of compounds of the formula (VI) where $R_6$ is hydrogen with a compound $R_2COCl$ in the presence of triethylamine or with $(R_2CO)_2O$ wherein $R_2$ is optionally substituted $C_{1-8}$ alkyl, $C_{2-8}$ alkenyl or aryl provides novel compounds of formula (X). Where $R_2$ is cyclopropyl, isobutyl or propionyl potencies comparable with that of Sufentanil may be provided.

(ii) N-acylation of compounds of the formula (VII) with compounds $(R_2CO)_2O$ or with $R_2COCl$ in the presence of triethylamine using the same procedure as described by Janssen gives compounds of formula (IX). Where $R_2$ is propyl R.30.490 results.

(iii) Where compound (VII) has $R_3$ value benzyl hydrogenation may be used to remove it to provide a compound of formula (VIII) allowing N-alkylation of the piperidine nitrogen with a 2-haloethyl-2-thiophene or 2-methanesulphonyl-oxyethyl-2-thiophene followed by N-propionylation as described by Janssen to provide sufentanil. The debenzylation may also be carried out, for example, by reaction with 2,2,2-trichloroethyl-orthoformate followed by reduction of the carbamate with zinc. Removal of a methyl protecting group may be carried out analogously using 2,2,2-trichloroethyl chloroformate.

(iv) N-acylation of compounds of the general formula (V) allows preparation of keto analogues of the Janssen patents as shown by formula (XI).

SYNTHESIS EXAMPLES

Example 1

2'-Phenylsulphinylspiro {1-(2-Phenylethyl)piperidinyl-4,1'-oxirane}

To a stirred solution of diisopropylamine (3.0 g, 30 mmol) in dry THF (20 ml), at −78° C. under nitrogen, was added a solution of n-butyllithium (20 ml of a 1.6M solution, 30 mmol) in hexane. After stirring for 30 min at −78° C., a solution of chloromethyl phenyl sulphoxide (2.75 g, 15 mmol) in dry THF (15 ml) was added dropwise. The mixture was stirred for a further 30 min at −78° C., and then 1-(2-phenylethyl)-4-piperidone (3 g, 15 mmol) in THF (15 ml) added dropwise. The reaction mixture was left for a further hour at −78° C. and then allowed to reach ambient temperature before pouring onto water. The aqueous mixture was extracted with ether, and the combined extracts washed, dried (over $MgSO_4$) and concentrated. Chromatography of the residue on silica gel using light petroleum-acetone 7:3 as eluant afforded 2'-phenylsulphinylspiro{1-(2-phenylethyl)piperidinyl-4,1'-oxirane} (2.4 g)

Example 2

4-(N-Phenylamino)-1-(2-phenylethyl)piperidine-4-carboxaldehyde

A mixture of 2'-phenylsulphinylspiro{1-(2-phenylethyl)piperidinyl-4,1'-oxirane} (2 g), aniline (5 ml) and two drops of dimethyl sulphoxide was stirred at room temperature for 16 hours. The reaction mixture was chromatographed directly onto silica gel using ether as an eluant to separate the crude reaction product from excess aniline, and then rechromatographed on silica gel, using petrol-ether 1:1 as eluant, to afford 4-(N-phenylamino)-1-(2-phenylethyl)piperidine-4-carboxaldehyde (1.56 g), m.p. 83°–84° C. after recrystallisation from petrol-ether.

Example 3

4-(N-phenylamino)-1-(2-phenylethyl)-4-piperidinylmethanol

Sodium borohydride (2 g) was added portionwise to a stirred solution of 4-(N-phenylamino)-1-(2-phenylethyl)piperidine-4-carboxaldehyde (2 g) in methanol (2 g) at room temperature for 2 hours. The mixture was diluted with water, extracted with chloroform and the combined extracts washed, dried over $MgSO_4$ and concentrated. The residue was chromatographed on silica gel, using chloroform-methanol 19:1 as eluant, to afford 4-(N-phenylamino)-1-(2-phenylethyl)-4-piperidinylmethanol (1.65 g), m.p. 98°–99° C.

Example 4

4-Methoxymethyl-4-(N-phenylamino)-1-(2-phenylethyl)piperidine

To a stirred mixture of 4-(N-phenylamino)-1-(2-phenylethyl)-4-piperidinylmethanol (0.100 g) and silica (0.5 g) in ether (5 ml) at room temperature was added an excess of ethereal diazomethane, and the mixture stirred at room temperature until no more colour remained. The reaction mixture was filtered and the filtrate concentrated to give an oil. Purification on silica gel using chloroform-methanol 38:1 as eluant gave the title compound (0.052 g).

Example 5

N-{4-methoxymethyl-1-(2-phenylethyl)-4-piperidnyl}-N-phenyl-propionanamide. (R.30.490.)

4-methoxymethyl-4-(N-phenylamino)-1-(2-phenylethyl)piperidine was reacted with propionic anhydride as described by the general method of U.S. Pat. No. 4,179,569.

Example 6

2'-Methyl-2'-phenylsulphinylspiro{1-(2-phenylethyl)-piperidinyl- 4,1'-oxirane}

To a stirred solution of diisopropylamine (3.0 g, 30 mmol) in dry THF (25 ml), at −78° C. under nitrogen, was added n-butyllithium (20 ml of a 1.6M solution in hexane, 30 mmol). After stirring for 15 min at −78° C. a solution of 1-chloroethyl phenyl sulphoxide (2.7 g, 14 mmol) in dry THF (10 ml) was added dropwise, the mixture stirred for a further 30 min at −78° C. and then N-(2-phenylethyl)-4-piperidone (3 g, 15 mmol) in THF (15 ml) added dropwise. The reaction mixture was left for a further 45 min at −78° C. and then allowed to reach ambient temperature before pouring onto water. The aqueous mixture was extracted with chloroform and the combined extracts washed, dried and concentrated. Chromatography of the residue on silica gel using petrol-acetone 7:3 as eluant gave 2'-methyl-2'-phenylsulphinylspiro{1-(2-phenylethyl)piperidinyl-4,1'-oxirane} (1.84 g) plus the intermediate chlorohydrin 4-{1-(1'-chloro-1'-phenylsulphinylethyl)}-1-(2-phenylethylpiperidin-4-ol)(0.92 g), m.p. 164°–166° C. To a solution of the chlorohydrin intermediate (0.500 g) in dry dimethylformamide (5 ml) at 0°–5° C. was added sodium hydride (0.60 g). The mixture was stirred for 30 minutes at 0°–5° C., allowed to regain room temperature and finally stirred for a further 30 minutes. The mixture was then diluted with water, extracted with ether, and the combined extracts washed, dried and concentrated. The reaction product was chromatographed on silica gel using chloroform-methanol 38:1 as eluant to give a further quantity of 2'-methyl-2'-phenylsulphinylspiro{1-(2-phenylethyl)piperidinyl-4,1'-oxirane} (0.310 g).

Example 7

1-}(4-Phenylamino)-1-(2-phenylethyl)-4-piperidinyl}ethanone

A mixture of 2'-methyl-2'-phenylsulphinylspiro{1-(2-phenylethyl) piperidinyl-4,1'-oxirane} (2.5 g) in aniline (5 ml) was stirred at 60° C. for 20 hours. The mixture was chromatographed directly on silica gel using ether as eluant to give 1-{4-phenylamino)-1-(2-phenylethyl)-4-piperidinyl}ethanone (2.03 g), m.p. 98°–99° C.

Example 8

N-{4-Acetyl-1-(2-phenylethyl)-4-piperidinyl}-N-phenylpropanamide

Was prepared from 1-{4-phenylamino)-1-(2-phenylethyl)-4-piperidinyl}ethanone by the method of Janssen.

Example 9

4-(1-hydroxyethyl)-4-(N-phenylamino)-1-(2-phenylethyl)piperidine

Sodium borohydride (0.500 g) was added portionwise to a stirred solution of 1-{(4-phenylamino)-1-(2-phenylethyl)-4-piperidinyl}ethanone (500 mg) in methanol (10 ml), keeping the temperature below 20° C. After stirring for 2 hours the reaction mixture was carefully diluted with water and extracted with ether. The combined extracts were washed, and concentrated and the residue was purified on silica gel using chloroform-methanol 19:1 as eluant to give the title compound (0.368 g).

Example 10

N-{4-(1-hydroxyethyl)-1-(2-phenylethyl)-4-piperidinyl}-N-phenyl-cyclopropylcarboxamide A solution of 4-(1-hydroxyethyl)-4-(N-phenylamino)-1-(2-phenylethyl)-piperidine (0.200 g), cyclopropylcarboxylic acid chloride (1 g) and triethylamine (2.2 g) in dry benzene (30 ml) was stirred for 2.5 hours at 60°–65° C. After cooling the mixture was washed with dilute sodium carbonate solution, dried over MgSO$_4$ and then concentrated. The residue was chromatographed on silica gel using chloroform-methanol 76:1 as eluant to give the title compound (0.160 g), which with oxalic acid gave an oxalate salt, m.p. 158°–159° C.

Example 11

2'-Phenylsulphinylspiro{1-phenylmethyl-piperidinyl-4,1'-oxirane} n-Butyllithium (14 ml of a 1.1M solution) in hexane was added dropwise to a solution of diisopropylamine (3.2 g) in dry tetrahydrofuran at −78° C. under nitrogen. After stirring for 30 min at −78° C., chloromethyl phenylsulphoxide (2.5 g) in tetrahydrofuran (10 ml) was added dropwise, the mixture stirred for a further 30 min at −78° C. and then a solution of 1-benzyl-4-piperidone (3 g) in dry tetrahydrofuran (10 ml) added dropwise. After stirring for a further 2 hours, the mixture was allowed to regain room temperature and, after stirring for a further hour, poured into water. The precipitate was filtered and recrystallised from methanol to yield the intermediate 4-{1'-chloro-1'-(phenylsulphinyl)methyl-1-phenylmethyl-piperidin-4-ol (1.9 g), m.p. 212° C. Sodium hydride (80% dispersion in oil, 1 g) was added portionwise to a stirred solution of the intermediate piperidinol (1.9 g) in dry dimethylformamide (10 ml) at 0° to 5° C. The solution was stirred for a further hour with ice bath cooling, then for 1 hour at room temperature and then poured into water. The mixture was then extracted with ether and the combined extracts washed with water and dried over MgSO$_4$. Concentration under reduced pressure and followed by chromatography of the residue on silica gel, using chloroform/methanol (38:1) as eluant gave the title compound (1.42 g) as a colourless oil.

Example 12

4-(N-phenylamino)-1-phenylmethyl-piperidine-4-carboxaldehyde

A mixture of the oxirane of Example 11 (0.6 g), aniline (0.6 g) and dimethyl sulphoxide (50 mg) was stirred at 45°–50° C. for 14 hours. The reaction mixture was separated by chromatography on silica gel, using chloroform/methanol (75:1) as eluant, and the crude product recrystallised from petroleum ether (b.p. 60°–80° C.) to give the title compound (0.416 g) m.p. 118°–119° C.

Example 13

2'-Phenylsulphinylspiro{1-methylpiperidinyl-4,1'-oxirane}

To a stirred solution of diisopropylamine (3 g) in dry tetrahydrofuran (20 ml) at −78° C. was slowly added n-butyllithium (20 ml of a 1.6M solution) in hexane, and the mixture stirred for an additional 30 min. a solution of chloromethyl methyl sulphoxide (2.5 g) in tetrahydrofuran (10 ml) was then added dropwise, and, after stirring for 30 min, N-methyl-4-piperidone (3.25 g) in tetrahydrofuran (10 ml) was added. After stirring for 1 hour at −78° C., the mixture was allowed to regain ambient temperature and stood overnight. The mixture was poured into water, extracted with ether and the combined extracts washed and dried. After removal of the solvent, the crude produce was chromatographed on silica gel, using chloroform/methanol (38:1) as eluant, to give the title compound (1.7 g) as a colourless oil.

Example 14

1-Methyl-4-(N-phenylamino)-piperidine-4-carboxaldehyde

A mixture of 2'-phenylsulphinylspiro-{1-methylpiperidinyl-4,1'-oxirane} (0.55 g), aniline (0.6 g) and dimethyl sulphoxide (0.05 g) was stirred at room temperature for 12 hours. The mixture was separated by chromatography on silica gel, using chloroform/methanol (38:1) as eluant, to give the title product as an oil (0.41 g).

Example 15

4-(N-phenylamino)-1-phenylmethyl-4-piperidinylmethanol

Figure 2:
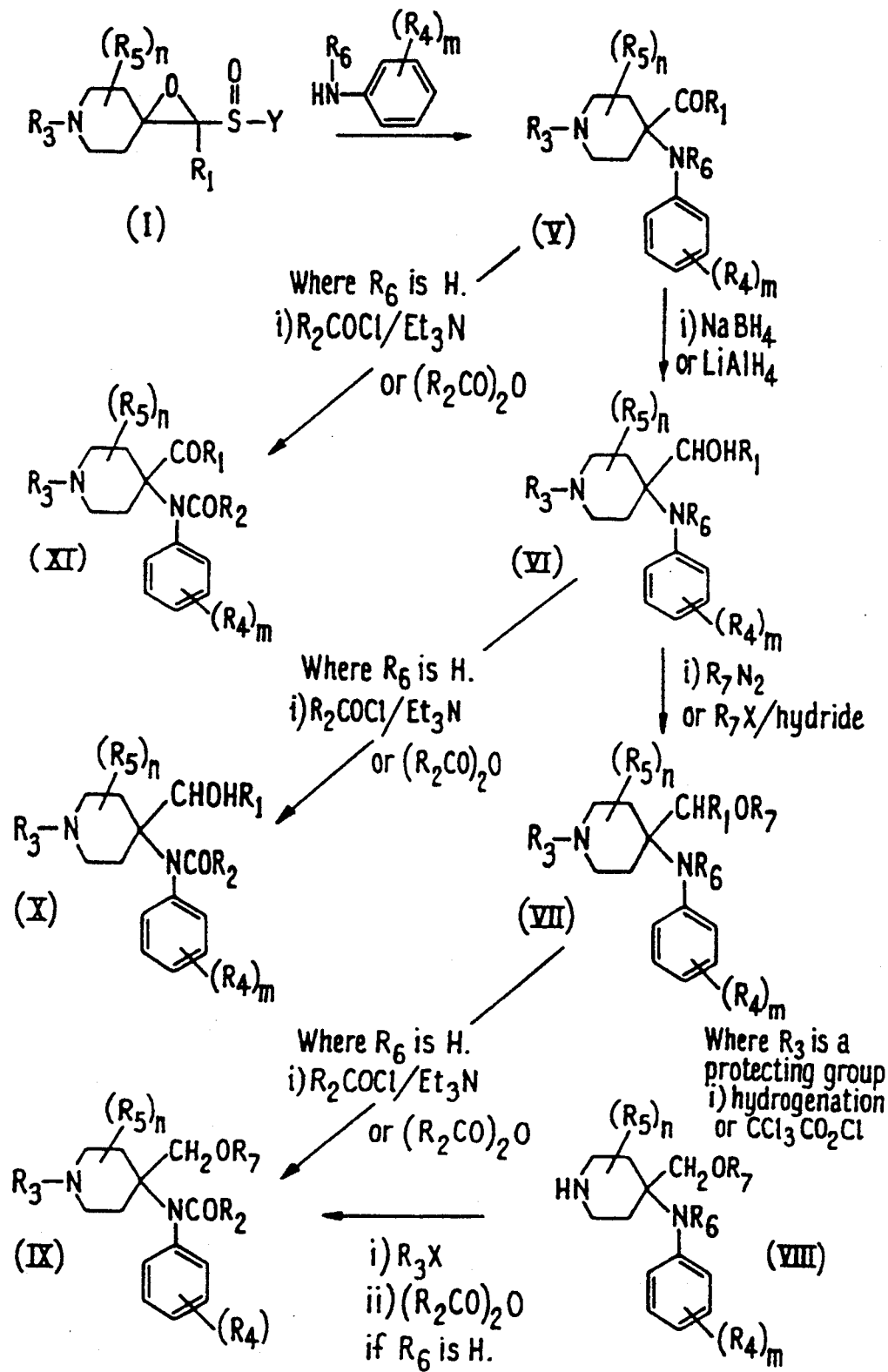

Sodium borohydride (2 g) was added portionwise to a stirred solution of 4-(N-phenylamino)-1-phenylmethyl-piperidine-4-carboxaldehyde (2 g) in methanol at room temperature. After stirring at room temperature for 2 hours the mixture was diluted with water, extracted with chloroform and the combined extracts washed and dried. After removal of the solvent, the crude product was purified by chromatography on silica gel, using chloroform/methanol (38:1) as eluant, to give the title compound (1.53 g) 4-(N-phenylamino)--1-phenylmethyl-4-piperidinylmethanol is then converted to sufentanil following the method described in U.S. Pat. No. 4,179,469 and as illustrated by FIG. 2.

Example 16

2'-Methyl-2'-phenylsulphonyl-{1-(2-phenylethyl)-piperidinyl-4,1'-oxirane}: Phase-transfer Synthesis of Compound of Formula I N-(2-phenylethyl)-4-piperidone (500 mg) and Aliquat 336 (tricaprylmethylammonium chloride) (100 mg) were added to a stirred solution of 1-chloroethyl phenyl sulphone (500 mg) in dichloromethane (20 ml) and the organic solution then stirred vigorously with 50% aqueous NaOH (5 ml) at ambient temperature for 8 hours. The organic layer was dried (MgSO$_4$), concentrated and purified over silica gel using light petroleum:acetone 8:2. The title compound was afforded as 385 mg of oil.

Example 17

1-{(4-phenylamino)-1-(2-phenylethyl)-4-piperidinyl}-ethanone

2'-methyl-2'-phenylsulphonyl{1-(2-phenylethyl)-piperidinyl-4,1'-oxirane} (100 mg) was stirred with aniline (400 mg) and a drop of dry dimethyl sulphoxide under nitrogen at 80°–85° C. for 20 hours. Chromatography over silica gel using light petroleum-acetone 7:3 as eluant afforded the title compound (66 mg).

REFERENCES

1. NIEMEGERS et al; ARZNEIM FORSCH 26 (1976), pp 1548.
2. ZHIJIE et al; PHARMACEUTICAL INDUSTRY 16 (1985), pp 241.

We claim:
1. A compound of the formula (I):

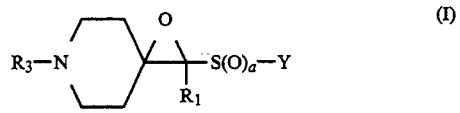

where
  R$_1$ is selected from the group consisting of hydrogen and C$_{1-3}$ alkyl;
  R$_3$ is selected from the group consisting of thienylethylene, phenylmethylene and phenylethylene;
  Y is selected from the group consisting of C$_{1-8}$ alkyl and aryl groups; and
  a is an integer 1 or 2.

2. The compound as claimed in claim 1 wherein Y is phenyl.

3. A compound as claimed in claim 1 selected from the group consisting of
  2'-phenylsulphinylspiro-{1-(2-phenylethyl)piperidinyl-4,1'-oxirane},
  2'-phenylsulphinylspiro-{1-phenylmethylpiperidinyl-4,1'-oxirane}, and
  2'-methyl-2'-2'-phenylsulphinylspiro-{1-(2-phenylethyl)-piperidinyl-4,1'-oxirane}.

4. 4-{1-(1'-chloro-1'-phenylsulphinyl)ethyl}-1-(2-phenylethylpiperidinol).

5. 4-{1'-chloro-1'(phenylsulphinyl)methyl}-1-phenylmethylpiperidi-4-ol.

6. N-{4-(1-hydroxyethyl)-1-(2-phenylethyl)-4-piperidinyl}-N-phenyl-cyclopropylcarboxamide.

* * * * *